(12) United States Patent
Yokoi

(10) Patent No.: US 9,400,245 B2
(45) Date of Patent: Jul. 26, 2016

(54) DRIFT CALCULATION DEVICE AND LIGHT DETECTION DEVICE PROVIDED WITH THE SAME

(71) Applicant: Shimadzu Corporation, Kyoto-shi, Kyoto (JP)

(72) Inventor: Yusuke Yokoi, Kyoto (JP)

(73) Assignee: SHIMADZU CORPORATION, Kyoto-shi (JP)

(*) Notice: Subject to any disclaimer, the term of this patent is extended or adjusted under 35 U.S.C. 154(b) by 0 days.

(21) Appl. No.: 14/440,660

(22) PCT Filed: Nov. 19, 2013

(86) PCT No.: PCT/JP2013/081142
§ 371 (c)(1),
(2) Date: May 5, 2015

(87) PCT Pub. No.: WO2014/091888
PCT Pub. Date: Jun. 19, 2014

(65) Prior Publication Data
US 2015/0300946 A1    Oct. 22, 2015

(30) Foreign Application Priority Data
Dec. 10, 2012 (JP) ................. 2012-269096

(51) Int. Cl.
*G01J 1/00* (2006.01)
*G01N 21/27* (2006.01)
(Continued)

(52) U.S. Cl.
CPC ............ *G01N 21/274* (2013.01); *G01J 1/0228* (2013.01); *G01J 1/4257* (2013.01); *G01N 30/8641* (2013.01); *G01J 2001/086* (2013.01); *G01J 2001/444* (2013.01)

(58) Field of Classification Search
USPC ............ 73/53.01, 61.61, 61.52, 61.57, 23.21, 73/23.2, 23.23, 23.25, 23.26; 210/198.2; 702/89; 356/121
See application file for complete search history.

(56) References Cited

U.S. PATENT DOCUMENTS 6,408,684 B1    6/2002    Bungo

FOREIGN PATENT DOCUMENTS

JP    61-218948 A    9/1986
JP    61-226659 A    10/1986
(Continued)

OTHER PUBLICATIONS

International Search Report dated Feb. 25, 2014, issued in corresponding application No. PCT/JP2013/081142.

*Primary Examiner* — Tri T Ton
(74) *Attorney, Agent, or Firm* — Westerman, Hattori, Daniels & Adrian, LLP

(57) ABSTRACT

There are provided a drift calculation device capable of accurately calculating a drift by using a buffer of smaller capacity, and a light detection device provided with the same. Every time measurement intensity is input according to a predetermined cycle, data in a plurality of sum buffers 321 to 324 are updated based on at least one of the measurement intensity and the measurement time at that time. The sum buffers 321 to 324 are assigned respectively to a plurality of sum functions forming a coefficient included in a calculation formula for calculating a drift by using the least squares method. A drift is calculated by substituting the updated data in the plurality of sum buffers 321 to 324 in the calculation formula. Since it is not necessary to store all the measurement intensity input at the predetermined cycle, a drift is accurately calculated by a buffer of smaller capacity.

7 Claims, 3 Drawing Sheets

(51) Int. Cl.
*G01N 30/86* (2006.01)
*G01J 1/42* (2006.01)
*G01J 1/02* (2006.01)
*G01J 1/44* (2006.01)
*G01J 1/08* (2006.01)

(56) References Cited

FOREIGN PATENT DOCUMENTS

| | | |
|---|---|---|
| JP | 2000-136999 A | 5/2000 |
| JP | 2002-55049 A | 2/2002 |

(a)

(b)

DRIFT CALCULATION DEVICE AND LIGHT DETECTION DEVICE PROVIDED WITH THE SAME

TECHNICAL FIELD

The present invention relates to a drift calculation device for calculating a drift based on measurement intensity that is input at a predetermined cycle, and a light detection device provided with the same.

BACKGROUND ART

For example, some analysis devices such as chromatographs are provided with a light detection unit including a plurality of light receiving elements, and measurement intensity is input to a control device at a predetermined cycle based on the received amount of measurement light at these light receiving elements. The control device is configured from a computer, for example, and is capable of acquiring, as measurement data, the relationship between the measurement intensity that is input at a predetermined cycle and the measurement time and of processing the measurement data.

With this type of analysis device, a change over time may occur in the measurement intensity because it takes time for the detection sensitivity to stabilize after the analysis is started, for example. Accordingly, some analysis devices adopt a configuration for performing, as an example of processing on the measurement data, calculation of the rate of change (drift) over time in the measurement intensity based on measurement data obtained by background measurement, and a process of correcting the measurement data based on the calculated drift (for example, see Patent Document 1).

FIGS. 3(a) and 3(b) are diagrams for describing conventional modes of calculation of a drift. In FIGS. 3(a) and 3(b), the relationship between the absorbance, which is an example of the measurement intensity, and the measurement time is partially shown as the measurement data.

In the example in FIG. 3(a), by determining a line L1 that is approximate to measurement data by using the least squares method, the slope of the line L1 is calculated as a drift D1. On the other hand, in the example in FIG. 3(b), arbitrary two points P1 and P2 are selected from measurement data and a line L2 that connects these two points P1 and P2 is determined to thereby calculate the slope of the line L2 as a drift D2.

PRIOR ART DOCUMENT

Patent Document

Patent Document 1: JP 2000-136999 A

SUMMARY OF THE INVENTION

Problems to be Solved by the Invention

In the case of calculating the drift D1 by the mode illustrated in FIG. 3(a), the drift D1 is calculated by using all of the measurement intensity that is input at a predetermined cycle within a specific period of time. To accurately calculate the drift D1, the specific period of time has to be set to a relatively long period of time, and is normally set to 60 to 90 minutes.

For example, in the case of calculating the drift D1 by using the measurement intensity obtained in 60 minutes at a frequency of 100 Hz, measurement intensity for 360000 times (100×60×60=360000) is used for each wavelength. Accordingly, if the data size for the measurement intensity for one time is 8 bytes, a buffer capacity of 2.88 Mbytes is required for each wavelength. If the number of light receiving elements is 1024, since the measurement intensity for a corresponding wavelength of each light receiving element is used, a large buffer capacity of 2949.12 Mbytes (2.88×1024) in total will be necessary.

Accordingly, with a device with a limited buffer capacity, there is a problem that a sufficient buffer capacity cannot be secured. Especially in the case of adopting a configuration for calculating the drift D1 at a light detection unit side (an analysis device side), for example, instead of adopting a configuration for inputting measurement data from a light detection unit to a control device and calculating the drift D1 at the control device, since it is difficult to provide a large-capacity buffer to the light detection unit side, the problem as described above becomes apparent.

Furthermore, in the case of calculating the drift D1 by the mode as illustrated in FIG. 3(a), the line L1 that is approximate to the measurement data cannot be determined by the least squares method until all of the measurement intensity (for 360000 times in the example described above) for each wavelength has been obtained. Accordingly, the processing load concentrates after the background measurement is ended, and problem such as a processing wait time may occur.

On the other hand, a problem as described above does not arise in the case of calculating the drift D2 by the mode as illustrated in FIG. 3(b). That is, since the drift D2 can be calculated by using the measurement intensity for two times for each wavelength, if the data size for the measurement intensity for one time is 8 bytes, it is enough if a buffer capacity of 16 bytes is secured for each wavelength. If the number of light receiving elements is 1024, the measurement intensity for two times becomes necessary for a corresponding wavelength of each light receiving element, but even then a relatively small buffer capacity of 16384 bytes in total will be sufficient.

However, with the mode as illustrated in FIG. 3(b), since the measurement intensity for only two times is used for each wavelength, there is a problem that the calculated drift D2 can hardly be said to be a highly accurate value. Especially, depending on the mode used at the time of selecting the two points P1 and P2 from the measurement data as the measurement intensity for two times, a great error may occur in the calculated drift D2, and the drift D2 is possibly not calculated with high accuracy.

The present invention has been made in view of the above circumstances, and has its aim to provide a drift calculation device capable of accurately calculating a drift using a buffer of a smaller capacity, and a light detection device provided with the same. Also, the present invention has its aim to provide a drift calculation device capable of preventing concentration of processing load at the time of calculation of a drift, and a light detection device provided with the same.

Means for Solving the Problems

A drift calculation device of the present invention is a drift calculation device for calculating a drift based on measurement intensity that is input at a predetermined cycle, the drift calculation device comprising: a plurality of sum buffers assigned respectively to a plurality of sum functions that take as a variable, with respect to a coefficient included in a calculation formula for calculating the drift by using a least squares method, at least one of measurement intensity and measurement time forming the coefficient; a data update unit for updating, every time the measurement intensity is input according to the predetermined cycle, data in the plurality of sum buffers based on at least one of the measurement intensity and the measurement time at the time; and a drift calculation unit for calculating the drift by substituting the data in the plurality of sum buffers updated by the data update unit in the calculation formula.

According to the configuration described above, every time the measurement intensity is input according to a predetermined cycle, the data in the plurality of sum buffers are updated based on at least one of measurement intensity and the measurement time at the time, and thus, it is not necessary to store all of the measurement intensity that is input at a predetermined cycle. Also, since the sum buffers are assigned to the sum functions forming the coefficient included in the calculation formula for calculating the drift by using the least squares method, the drift may be accurately calculated by substituting the updated data in the sum buffers in the calculation formula. Accordingly, the drift may be accurately calculated by using a buffer with a smaller capacity.

Also, the data in the plurality of sum buffers are updated every time the measurement intensity is input according to a predetermined cycle, based on at least one of the measurement intensity and the measurement time at the time, and after all of the measurement intensity has been input, the updated data in each of the sum buffers is simply substituted in the calculation formula. Accordingly, compared to a configuration where the process for calculating a drift is started after all of the measurement intensity input at a predetermined cycle has been obtained, the processing may be distributed, and the processing load may be prevented from concentrating at the time of calculating a drift.

The drift calculation device may further comprise a shared buffer assigned to a variable that may be used in common by the plurality of sum functions. In this case, the data update unit may update data in the shared buffer every time the measurement intensity is input according to the predetermined cycle. Also, the drift calculation unit may calculate the drift by substituting the data in the plurality of sum buffers and the shared buffer updated by the data update unit in the calculation formula.

According to the configuration described above, the shared buffer which is assigned to the variable which may be used commonly in the plurality of sum functions is used, and thus, the drift may be accurately calculated by using a buffer with an even smaller capacity.

A light detection device of the present invention comprises the drift calculation device; and a light detection unit for inputting measurement intensity based on a received amount of measurement light to the drift calculation device at a predetermined cycle.

According to the configuration described above, a light detection device capable of accurately calculating a drift by using a buffer with a smaller capacity and of preventing the processing load from concentrating at the time of calculating a drift may be provided. In the case of a configuration where the drift is calculated at the light detection device, as described above, data that is based on the calculated drift may be checked on a display unit or the like of the light detection device.

Accordingly, for example, in the case of working near the light detection device, the burden of having to check data that is based on the calculated drift at another device (a control device or the like) may be eliminated, and the work may be smoothly performed. Also, in the case where it is difficult to provide a large-capacity buffer to the light detection device, a buffer capacity sufficient to calculate a drift may be secured by enabling accurate calculation of the drift by using a buffer with a smaller capacity as in the case described above.

Effects of the Invention

According to the present invention, it is not necessary to store all of the measurement intensity that is input at a predetermined cycle, and the sum buffers are assigned to the sum functions forming a coefficient included in the calculation formula for calculating the drift by using the least squares method, and thus, the drift may be accurately calculated by using a buffer of a smaller capacity.

Also, according to the present invention, the data in the plurality of sum buffers are updated every time the measurement intensity is input according to a predetermined cycle, based on at least one of the measurement intensity and the measurement time at the time, and after all of the measurement intensity has been input, the updated data in each of the sum buffers is simply substituted in the calculation formula, and thus the processing may be distributed, and the processing load may be prevented from concentrating at the time of calculating a drift.

MODE FOR CARRYING OUT THE INVENTION

Figure 1:
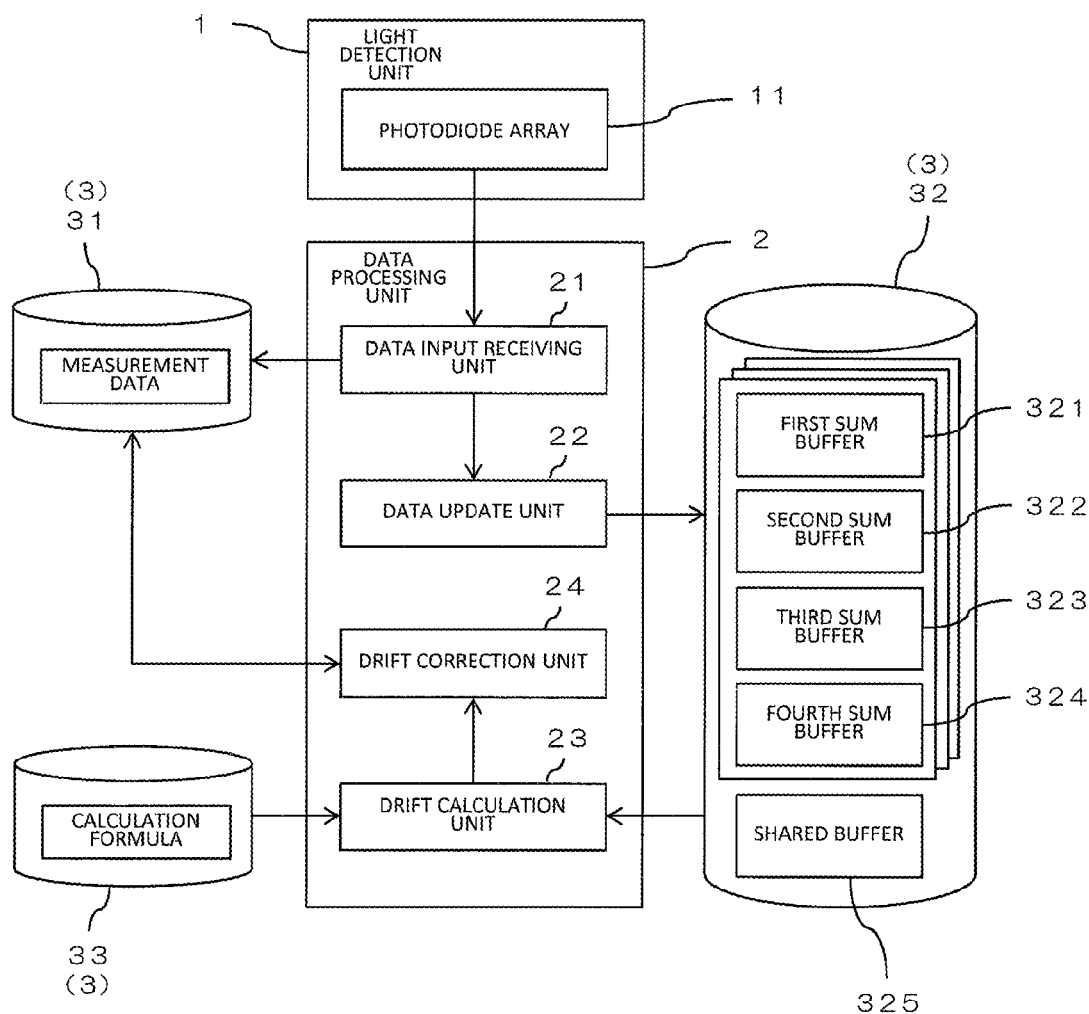
FIG. 1 is a block diagram showing a configuration example of a light detection device according to an embodiment of the present invention.

FIG. 1 is a block diagram showing a configuration example of a light detection device according to an embodiment of the present invention. This light detection device is used for an analysis device such as a chromatograph, and is provided with a light detection unit 1, a data processing unit 2, a storage unit 3, and the like. However, the light detection device according to the present embodiment may also be applied to analysis devices other than the chromatograph.

The light detection unit 1 is provided with a photodiode array 11 including a plurality of photodiodes as light receiving elements, for example. At the time of analyzing a sample, the measurement light from the sample is received by the photodiode array 11, and the measurement intensity for each wavelength may be obtained based on the amount of received light at each light receiving element. Incidentally, the light detection unit 1 is not limited to be configured from a photodiode array, and may alternatively be configured from a different detector such as an UV detector, for example.

The data processing unit 2 has a structure including a CPU (Central Processing Unit), for example. The data processing unit 2 functions as various functional units such as a data input receiving unit 21, a data update unit 22, a drift calculation unit 23, a drift correction unit 24, and the like by the CPU executing programs. The data processing unit 2 may also be configured from various logic circuits as exemplified by a CPLD (Complex Programmable Logic Device), for example.

The storage unit 3 may be configured from a RANI (Random Access Memory), a ROM (Read-Only Memory), and the like, for example. A measurement data storage unit 31, a storage unit 32 for drift calculation, a calculation formula storage unit 33, and the like are assigned to the storage unit 3.

Measurement intensity based on the amount of received light at the light detection unit 1 is input to the data processing unit 2 at a predetermined cycle, and measurement data indicating the relationship between the measurement intensity and the measurement time is stored in the measurement data storage unit 31.

With the analysis device, a change over time may occur in the measurement intensity because it takes time for the detection sensitivity to stabilize after the analysis is started, for example. The light detection device according to the present embodiment is able to calculate the rate of change (drift) over time in the measurement intensity, and to correct the measurement data based on the calculated drift.

A drift may be calculated based on measurement intensity that is input at a predetermined cycle at the time of performing measurement in a state where there is no sample (so-called background measurement), for example. Then, by correcting, by using the calculated drift, the measurement data that is obtained at the time of actually analyzing a sample, measurement data from which the influence of a drift is removed or alleviated may be obtained.

A plurality of buffers that are used at the time of calculating the drift are assigned to the storage unit 32 for drift calculation. Also, a calculation formula that is used at the time of calculating the drift is stored in the calculation formula storage unit 33. In the present embodiment, the data processing unit 2, the storage unit 32 for drift calculation, and the calculation formula storage unit 33 configure the drift calculation device for calculating the drift based on the measurement intensity that is input at a predetermined cycle. This drift calculation device is able to calculate the drift by using the least squares method.

Specifically, in the case of determining, with respect to measurement data indicating the relationship between the measurement intensity and the measurement time, a line that is approximate to the measurement data by using the least squares method, a slope a of a line and an intercept b may be expressed by the following formula (1) where the measurement intensity is $y_i$ and the measurement time is $x_i$.

[Math. 1]

$$\text{Slope } a = \frac{n\sum_{i=1}^{n} x_i y_i - \sum_{i=1}^{n} x_i \sum_{i=1}^{n} y_i}{n\sum_{i=1}^{n} x_i^2 - \left(\sum_{i=1}^{n} x_i\right)^2}$$

$$\text{Intercept } b = \frac{n\sum_{i=1}^{n} x_i^2 y_i - \sum_{i=1}^{n} x_i y_i \sum_{i=1}^{n} x_i}{n\sum_{i=1}^{n} x_i^2 - \left(\sum_{i=1}^{n} x_i\right)^2} \quad (1)$$

Now, a drift is the amount of change in the measurement intensity per unit time, and is not related to the value of the intercept b and may be calculated from the value of the slope a. Thus, in the present embodiment, with respect to the slope a, which is a coefficient included in the calculation formula for calculating the drift using the least squares method, a sum buffer is assigned to each of the following four sum functions (2-1) to (2-4) forming the slope a.

[Math. 2]

$$\sum_{i=1}^{n} x_i y_i \quad (2\text{-}1)$$

$$\sum_{i=1}^{n} x_i^2 \quad (2\text{-}2)$$

$$\sum_{i=1}^{n} x_i \quad (2\text{-}3)$$

$$\sum_{i=1}^{n} y_i \quad (2\text{-}4)$$

That is, the storage unit 32 for drift calculation includes four sum buffers 321 to 324 assigned respectively to the four sum functions (2-1) to (2-4) which take at least one of the measurement intensity $y_i$ and the measurement time $x_i$ forming the slope a as the variable. The first sum buffer 321 is associated with the sum function (2-1), the second sum buffer 322 is associated with the sum function (2-2), the third sum buffer 323 is associated with the sum function (2-3), and the fourth sum buffer 324 is associated with the sum function (2-4).

These sum buffers 321 to 324 are provided for respective wavelengths to be measured. Also, the storage unit 32 for drift calculation includes a shared buffer 325 which is assigned to a variable n which may be used commonly in the four sum functions (2-1) to (2-4). The data in this shared buffer 325 is incremented (+1) every time the measurement intensity $y_i$ is input according to a predetermined cycle. Accordingly, in the case of calculating the drift by using the measurement intensity that is obtained in 60 minutes at a frequency of 100 Hz, for example, the final value of the variable n will be 360000.

The data input receiving unit 21 receives input of data of the measurement intensity $y_i$ from the photodiode array 11 of the light detection unit 1. The measurement intensity $y_i$ is input to the data input receiving unit 21 at a predetermined cycle, and the relationship between the measurement intensity $y_i$ that is input at a predetermined cycle and the measurement time $x_1$ is stored in the measurement data storage unit 31 as measurement data. Also, every time the measurement intensity $y_i$ is input to the data input receiving unit 21 according to a predetermined cycle, the measurement intensity $y_i$ and the measurement time $x_i$ at the time are input to the data update unit 22.

Every time the measurement intensity $y_i$ is input according to a predetermined cycle, the data update unit 22 updates the sum buffers 321 to 324 based on at least one of the measurement intensity $y_i$ and the measurement time $x_1$ at the time, and also, updates (increments) the data in the shared buffer 325. Specifically, the first sum buffer 321 is updated based on both the measurement intensity $y_i$ and the measurement time $x_i$, the second and the third sum buffers 322 and 323 are updated based on the measurement time $x_i$, and the fourth sum buffer 324 is updated based on the measurement intensity $y_i$.

At this time, each of the sum buffers 321 to 324 is updated by being sequentially added with a value that is based on at least one of the measurement intensity $y_i$ and the measurement time That is, the first sum buffer 321 is updated by being added at a predetermined cycle with a value of $x_i y_i$, the second sum buffer 322 is updated by being added at a predetermined cycle with a value of $x_i^2$, the third sum buffer 323 is updated by being added at a predetermined cycle with a value of $x_i$, and the fourth sum buffer 324 is updated by being added at a predetermined cycle with a value of $y_i$.

The drift calculation unit 23 calculates a drift by substituting the data in each of the sum buffers 321 to 324 and the shared buffer 325 updated by the data update unit 22 in the calculating formula stored in the calculation formula storage unit 33. The slope a described above is included, as a coefficient, in the calculating formula stored in the calculation formula storage unit 33, and the data (final values) of the sum buffers 321 to 324 are substituted in the four sum functions (2-1) to (2-4) described above forming the slope a, and the data (final value) in the shared buffer 325 is substituted as the variable n.

A drift calculated in the above manner is used at the time of drift correction performed by the drift correction unit 24. The drift correction unit 24 performs a correction process based on the drift calculated by the drift calculation unit 23 on the measurement data that is stored in the measurement data storage unit 31 by actually analyzing a sample.

Figure 2:
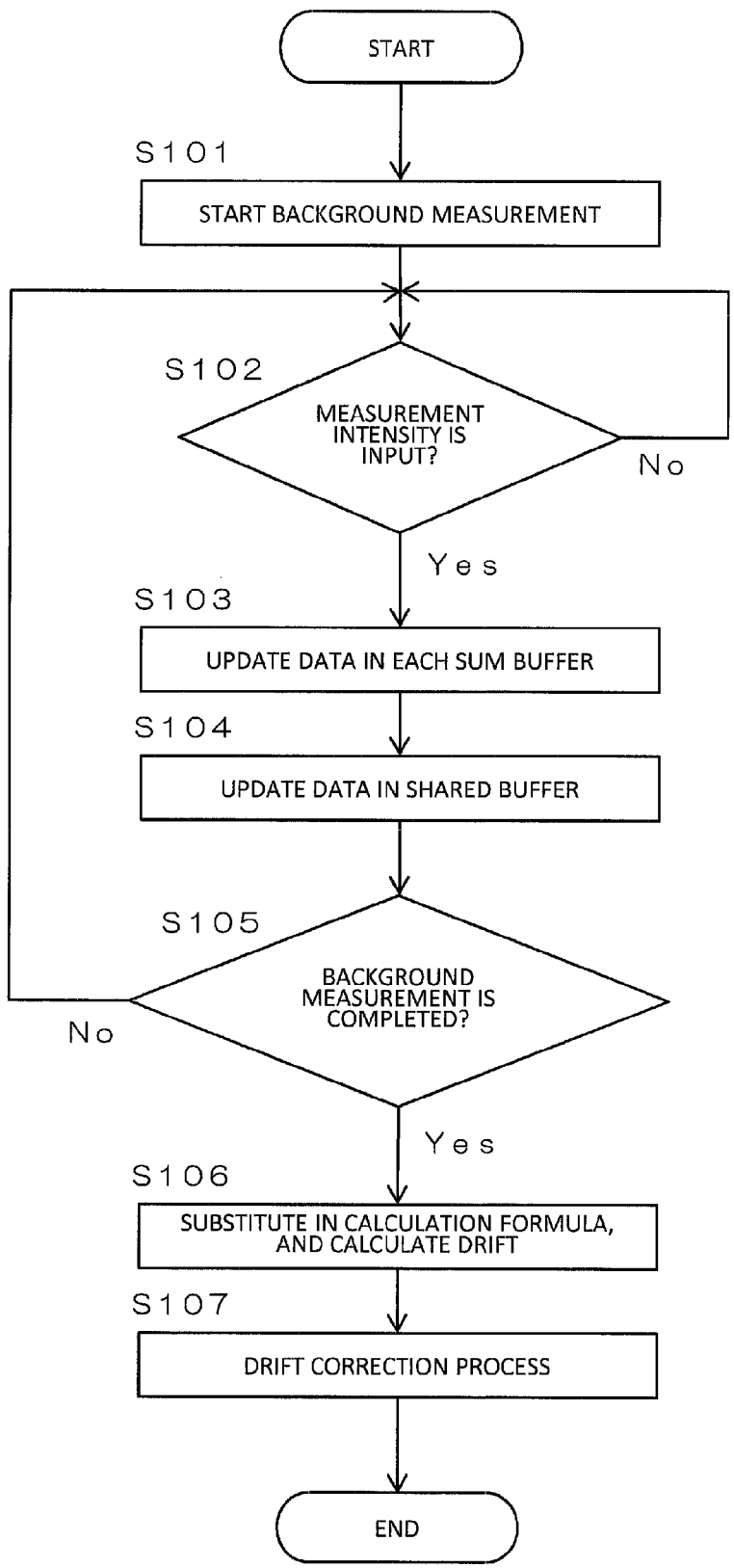
FIG. 2 is a flow chart showing an example of a process by a data processing unit.

FIG. 2 is a flow chart showing an example of a process by the data processing unit 2. At the time of performing a process for calculating a drift, first, background measurement is started (step S101).

During the background measurement, every time the measurement intensity $y_i$ is input from the light detection unit 1 according to a predetermined cycle (Yes in step S102), the process for updating the data in each of the sum buffers 321 to 324 (step S103) and the process for updating the data in the shared buffer 325 (step S104) are performed.

The process in step S103 is performed for all the wavelengths by using the sum buffers 321 to 324 provided for respective wavelengths.

Then, after the background measurement is completed (Yes in step S105), the drift is calculated by the data in each of the sum buffers 321 to 324 and the shared buffer 325 being substituted in the calculation formula (step S106). Then, a correction process based on the calculated drift is performed on measurement data that is obtained by actually analyzing a sample (step S107). Incidentally, the drift correction does not have to be performed together with the process for calculating the drift, and it may be performed at an arbitrary timing using the calculated drift.

In the present embodiment, every time the measurement intensity $y_i$ is input according to a predetermined cycle, the data in the plurality of sum buffers 321 to 324 are updated based on at least one of measurement intensity $y_i$ and the measurement time $x_1$ at the time, and thus, it is not necessary to store all of the measurement intensity $y_i$ that is input at a predetermined cycle. Also, since the sum buffers 321 to 324 are assigned to the sum functions (2-1) to (2-4) forming the coefficient (the slope a) included in the calculation formula for calculating the drift by using the least squares method, the drift may be accurately calculated by substituting the updated data in the sum buffers 321 to 324 in the calculation formula. Accordingly, the drift may be accurately calculated by using a buffer with a smaller capacity.

Particularly, in the present embodiment, the shared buffer 325 which is assigned to the variable n which may be used commonly in the plurality of sum functions (2-1) to (2-4) is used, and thus, the drift may be accurately calculated by using a buffer with an even smaller capacity.

Figure 3:
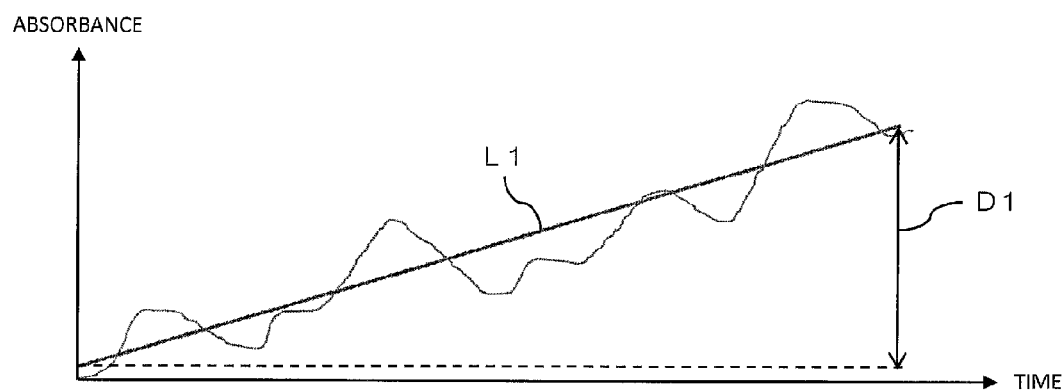
FIGS. 3(a) and 3(b) are diagrams for describing conventional modes of calculation of a drift.
Figure 3:
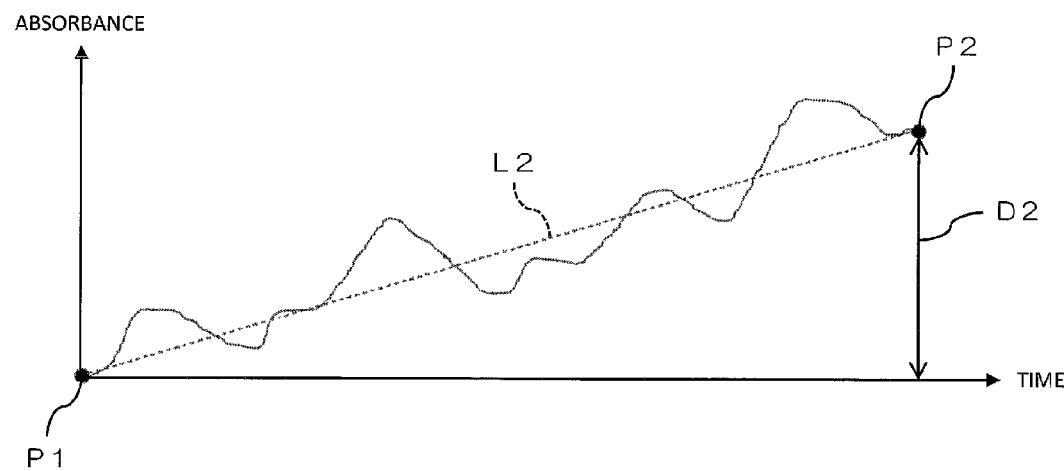

For example, in the case of performing measurement by 1024 light receiving elements by using four sum buffers 321 to 324 and one shared buffer 325, as in the present embodiment, if the capacity of each of the sum buffers 321 to 324 is 8 bytes and the capacity of the shared buffer 325 is 4 bytes, the required buffer capacity is 32772 bytes (1024×4×8+1×4). This value is significantly smaller than the buffer capacity (2949.12 Mbytes) required for calculating the drift D1 by the mode as illustrated in FIG. 3(a).

Also, in the present embodiment, the data in the plurality of sum buffers 321 to 324 are updated every time the measurement intensity $y_i$ is input according to a predetermined cycle, based on at least one of the measurement intensity $y_i$ and the measurement time $x_1$ at the time, and after all of the measurement intensity $y_i$ has been input, the updated data in each of the sum buffers 321 to 324 is simply substituted in the calculation formula. Accordingly, compared to a configuration where the process for calculating a drift is started after all of the measurement intensity $y_i$ input at a predetermined cycle has been obtained, the processing may be distributed, and the processing load may be prevented from concentrating at the time of calculating a drift.

In the case where the drift calculation device and the light detection device are integrally structured as in the present embodiment, data that is based on the calculated drift may be checked on a display unit (not shown) or the like of the light detection device, for example.

Accordingly, for example, in the case of working near the light detection device, the burden of having to check data that is based on the calculated drift at another device (the control device or the like) may be eliminated, and the work may be smoothly performed. Also, in the case where it is difficult to provide a large-capacity buffer to the light detection device, a buffer capacity sufficient to calculate a drift may be secured by enabling accurate calculation of the drift by using a buffer with a smaller capacity as in the case described above.

Note that the drift calculation device according to the present invention is not limited to be integrally structured with the light detection device, and it is also possible to separately provide the drift calculation device. In this case, by connecting the light detection device to the drift calculation device, the measurement intensity may be input to the drift measurement device at a predetermined cycle from the light detection unit 1 of the light detection device.

Also, the calculation formula for calculating the drift is not limited to the one as described above including the slope a as the coefficient. That is, the plurality of sum buffers are not limited to the sum buffers 321 to 324 as described above assigned to the four sum functions (2-1) to (2-4), respectively, and may be those assigned to other sum functions. Thus, the number of sum buffers is not limited to four. Also, the shared buffer 325 may be omitted, and an output value from a counting unit such as a counter may be substituted in the calculation formula.

DESCRIPTION OF REFERENCE SIGNS 1 light detection unit
2 data processing unit
3 storage unit
11 photodiode array
21 data input receiving unit
22 data update unit
23 drift calculation unit
24 drift correction unit
31 measurement data storage unit
32 storage unit for drift calculation
33 calculation formula storage unit
321 first sum buffer
322 second sum buffer
323 third sum buffer
324 fourth sum buffer
325 shared buffer

The invention claimed is:

1. A drift calculation device for calculating a drift based on measurement intensity that is input at a predetermined cycle, the drift calculation device comprising:
a plurality of sum buffers assigned respectively to a plurality of following sum functions that take as a variable, with respect to a coefficient included in a following calculation formula for calculating the drift by using a least squares method, at least one of measurement intensity and measurement time forming the coefficient;

$$\left. \begin{array}{l} \text{Slope } a = \dfrac{n\sum_{i=1}^{n} x_i y_i - \sum_{i=1}^{n} x_i \sum_{i=1}^{n} y_i}{n\sum_{i=1}^{n} x_i^2 - \left(\sum_{i=1}^{n} x_i\right)^2} \\ \\ \text{Intercept } b = \dfrac{n\sum_{i=1}^{n} x_i^2 y_i - \sum_{i=1}^{n} x_i y_i \sum_{i=1}^{n} x_i}{n\sum_{i=1}^{n} x_i^2 - \left(\sum_{i=1}^{n} x_i\right)^2} \end{array} \right\} \quad (1)$$

$$\sum_{i=1}^{n} x_i y_i \quad (2\text{-}1)$$

$$\sum_{i=1}^{n} x_i^2 \quad (2\text{-}2)$$

$$\sum_{i=1}^{n} x_i \quad (2\text{-}3)$$

$$\sum_{i=1}^{n} y_i \quad (2\text{-}4)$$

wherein $x_1$ is the measurement time, $v_1$ is measurement intensity;

a data update unit for updating, every time the measurement intensity is input according to the predetermined cycle, data in the plurality of sum buffers based on at least one of the measurement intensity and the measurement time at the time; and
a drift calculation unit for calculating the drift by substituting the data in the plurality of sum buffers updated by the data update unit in the calculation formula.

2. The drift calculation device according to claim 1, further comprising:
a shared buffer assigned to a variable that may be used in common by the plurality of sum functions,
wherein the data update unit updates data in the shared buffer every time the measurement intensity is input according to the predetermined cycle, and
wherein the drift calculation unit calculates the drift by substituting the data in the plurality of sum buffers and the shared buffer updated by the data update unit in the calculation formula.

3. A light detection device comprising:
the drift calculation device according to claim 1; and
a light detection unit for inputting measurement intensity based on a received amount of measurement light to the drift calculation device at a predetermined cycle.

4. A light detection device comprising:
the drift calculation device according to claim 2; and
a light detection unit for inputting measurement intensity based on a received amount of measurement light to the drift calculation device at a predetermined cycle.

5. The drift calculation device according to claim 1, wherein measurement intensity forms the coefficient.

6. The drift calculation device according to claim 1, wherein measurement time forms the coefficient.

7. The drift calculation device according to claim 1, wherein measurement intensity and measurement time form the coefficient.

* * * * *